US005691203A

United States Patent [19]
Katsuen et al.

[11] Patent Number: 5,691,203
[45] Date of Patent: Nov. 25, 1997

[54] METHOD FOR SERUM-FREE CULTURE OF HUMAN VASCULAR ENDOTHELIAL CELLS

[75] Inventors: Susumu Katsuen; Kunihiro Ohshima, both of Osaka; Ryohei Yamamoto, Takatsuki; Toyokazu Nishino, Ibaraki, all of Japan

[73] Assignee: Kurashiki Boseki Kabushiki Kaisha, Kurashiki, Japan

[21] Appl. No.: 128,225

[22] Filed: Sep. 29, 1993

[30] Foreign Application Priority Data

Jun. 14, 1993 [JP] Japan ................. 5-141984

[51] Int. Cl.$^6$ ................. C12N 5/00; C12N 11/00; C12N 11/02; C12N 11/08
[52] U.S. Cl. ................. 435/402; 435/177; 435/180; 435/366; 435/395; 435/396; 435/404; 435/407
[58] Field of Search ................. 435/240, 243, 435/174, 177, 180, 402, 366, 395, 396, 404, 407

[56] References Cited

U.S. PATENT DOCUMENTS

| | | | |
|---|---|---|---|
| 5,202,227 | 4/1993 | Matsuda et al. | 435/240.243 X |
| 5,232,848 | 8/1993 | Wolfe et al. | 435/240.31 |
| 5,276,136 | 1/1994 | Skubitz et al. | 530/326 |
| 5,278,063 | 1/1994 | Habbell et al. | 435/240.243 X |
| 5,284,766 | 2/1994 | Okano et al. | 435/240.243 X |

OTHER PUBLICATIONS

Ann Knedler et al., "Optimized Medium for clonal Growth of Human Microvascular Endothelial Cells with Minimal Serum", In Vitro Cellular & Developmental Biology, vol. 23, No. 7, pp. 481-491, (1987).

Hirano et al., Journal of Biomedical Materials Research, vol. 25, 1991, pp. 1523-1534.

Milhausen, S., J. Cell Physiol., vol. 96, 1978, pp. 1-14.

Primary Examiner—David M. Naff
Attorney, Agent, or Firm—Foley & Lardner

[57] ABSTRACT

Animal adhesive cells, particularly human vascular endothelial cells, are cultured in serum-free condition by coating at least one polymer having cell adhesive activity on an inner surface of a culture vessel or surface of a carrier for cell culture, and culturing the cells in the coated vessel or with the coated carrier using a serum-free medium for animal cell culture containing isolated serum albumin, and preferably also transferrin. The polymer is a synthetic polymer modified with a peptide having cell adhesive activity or a natural polymer having cell adhesive activity or a combination thereof. Preferably, the peptide is RGDV, RGDS, RGDN, DGEA or YIGSR and the natural polymer is collagen, gelatin, keratin, fibronectin, vitronectin or laminin. A preferred medium for culturing human vascular endothelial cells is basal medium MCDB 131 or MCDB 107 containing isolated serum albumin, transferrin, hydrocortisone and epithelial growth factor.

5 Claims, 1 Drawing Sheet

Fig.1 ns*

METHOD FOR SERUM-FREE CULTURE OF HUMAN VASCULAR ENDOTHELIAL CELLS

BACKGROUND OF THE INVENTION

1. Field of the Invention

The present invention relates to a method for culturing animal adhesive cells, especially vascular endothelial cells in serum-free condition.

2. Prior Art

The vascular endothelial cell plays an important role in vascularization and in such a vascular lesion as arteriosclerosis, and its proliferation and differentiation have been extensively studied. Studies on such physiologically active substances as endothelin, interleukins, colony-stimulating factor and prostaglandins, which are produced by vascular endothelial cells, have also been done extensively. For such investigations it is essential to culture the cells in vitro.

However, since such animal adhesive cells as vascular endothelial cells would not grow without their adhesion to inner surface of a culture vessel, a medium containing about 10% of fetal bovine serum, calf serum or other serum is generally used for culture of the cell. A serum contains numerous substances including vitronectin that has the property of making cells adhere onto objects, therefore the animal adhesive cells in a culture medium can adhere onto the inner surface of a culture vessel, spread and grow.

The serum cannot be produced in bulk and therefore is very expensive. Further, due to large differences in its composition among individual animals (lot differences) and limited amounts of one lot, troublesome operations would be involved for the lot check, adjustment and administration of culture conditions, and the like whenever the lot is changed. Furthermore, since a serum is a mixture of numerous substances with physiological activities which are produced by blood cells and vascular endothelial cell, a high level of purification procedure is required for the analysis and utilization of the products obtained from the cells cultured in an serum-containing medium. To solve these problems, there has been a desire for culture of animal adhesive cells, especially vascular endothelial cells under serum-free conditions.

Previously several methods for serum-free culture of vascular endothelial cells have been proposed. Examples reported are a method for culture of a vascular endothelial cells in a serum-free medium to which is added heparin or cell growth factor (see Japanese Patent Laid-Open Publication No. 187083/1989), and in a serum-free medium to which is added zinc or copper salt (see Japanese Patent Laid-Open Publication No. 97379/1990).

SUMMARY OF THE INVENTION

The present invention has been carried out in order to provide a method for culturing animal adhesive cells, particularly of vascular endothelial cells, in serum-free condition, which enhances the adhesive property and growth of the cells in serum-free condition.

According to the present of invention, there is provided a method for culturing animal adhesive cells in serum free condition comprising 1) coating one or more polymer having cell adhesive activity on at least a part of inner surface of a culture vessel or surface of a carrier for cell culture, and 2) culturing animal adhesive cells in the vessel or with the carrier using a serum-free medium for animal cell culture containing at least serum albumin. By the method of the present invention it is now possible to do culture of animal adhesive cells, particularly vascular endothelial cells, in serum-free condition easily. The cells cultured by the method of the present invention keeps similar functions to the cell cultured in a medium containing serum.

DETAILED DESCRIPTION OF THE INVENTION

The method for culturing animal adhesive cells in serum free condition in the present invention comprising 1) coating one or more polymer having cell adhesive activity on at least a part of inner surface of a culture vessel or surface of a carrier for cell culture, and 2) culturing animal adhesive cells in the vessel or in the presence of the carrier using a serum-free medium for animal cell culture containing at least serum albumin.

The polymer having cell adhesive activity in the present invention may be any natural or synthetic polymer which has the activity of making cells adhere to objects. The polymer may also be a mixture of both polymers.

Preferably, the natural polymers having cell adhesive activity include collagen, gelatin, keratin, fibronectin, vitronectin and laminin. These polymers are obtained from extracellular matrix components and they all are known to have the cell adhesive activity. They show different adhesion characteristics from one another, and it is advised to select a polymer depending on animal species, organ and site of vessel from which the cell to be cultured is derived. For example, in the case of human umbilical vein endothelial cells, collagen type I is preferably employed.

Examples of the synthetic polymer having cell adhesive activity include the polymers chemically modified with peptides having cell adhesive activity and polymers with positive charges. In particular, the water insoluble polymers chemically modified with peptides having cell adhesive activity may be used preferably.

Many of peptides having cell adhesive activity (cell adhesive peptides) have now been known from the analysis of the active site of proteins having cell adhesive activity such as fibronectin or laminin. The peptide to be employed in the invention may be any that has cell adhesive activity, and any known one may be selected according to the kind of cell to be cultured.

Examples of the cell adhesive peptide that used in the present invention are RGDV (Arg-Gly-Asp-Val), RGDS (Arg-Gly-Asp-Ser), RGDN (Arg-Gly-Asp-Asn), DGEA (Asp-Gly-Glu-Ala) and YIGSR (Tyr-Ile-Gly-Ser-Arg). These peptides may be synthesized from respective amino acids by conventional methods.

In this specification, amino acids, peptides and protective groups are shown by the following abbreviations:

| | |
|---|---|
| Ala: L-alanine | Glu: L-glutamic acid |
| Arg: L-arginine | Gly: L-glycine |
| Asn: L-asparagine | Ser: L-serine |
| Asp: L-aspartic acid | Tyr: L-tyrosine |
| Ile: L-Isoleucine | Val: L-valine |
| Boc: t-butyloxycarbonyl | OBzl: benzyl |
| OcHex: cyclohexyl | Tos: tosyl |

The polymer chemically modified with a cell adhesive peptide may be obtained by copolymerization of a monomer prepared by reacting the peptide with an appropriate polymerizable monomer, and another polymerizable monomer.

Examples of the monomer to be reacted with a cell adhesive peptide include (meth)acrylic acid, (meth)acrylamide, glycidyl (meth)acrylate, N-(meth)-acryloyloxysuccinimide. The other polymerizable monomer to be copolymerized with the monomer chemically modified with a cell adhesive peptide is exemplified by: hydrophilic monomers such as hydroxyethyl (meth)acrylate, hydroxypropyl (meth)acrylate, glycerol (meth)acrylate, pentaerythritol (meth)acrylate, oligoethylene glycol (meth)acrylate and oligopropylene glycol (meth)acrylate and mixtures thereof; and hydrophobic monomers such as methyl (meth)acrylate, ethyl (meth)acrylate, n-propyl (meth)acrylate, isopropyl (meth)acrylate, n-butyl (meth)acrylate, isobutyl (meth) acrylate and t-butyl (meth)acrylate and mixtures thereof. It is noted that the term "(meth)acrylate" herein denotes "acrylate" and "methacrylate".

According to the present invention, it is desirable to introduce a cell adhesive peptide into the polymer in a ratio higher than 2 µg/mg. When the amount of the cell adhesive peptide is less than 2 µg/mg, coating of the inner surface of a culture vessel with such polymer will not sufficiently effect the adhesion of the cultured cells so that effective growth of the cells cannot be expected.

Since the cell adhesive potency of the peptides shows some specificity, by which purification of the cells to be cultured can be achieved. For example, in the culture of vascular endothelial cells, vascular smooth muscle cells that are present as contaminant can be removed from the culture.

In the method of the present invention, one or more of the natural or synthetic polymers as described above may be employed. By using a mixture of the both types of polymers for coating on the inner surface of culture vessel, higher adhesion and growth of the cells can be obtained. The preferable mixing ratio of both polymers is 1:9–9:1, and a ratio of 1:1 is particularly preferable.

According to the present invention, for coating of the polymers on the inner surface of a culture vessel, it is preferable to apply a solution or suspension in which one or more of the above natural or synthetic polymers has been dissolved or suspended in an appropriate solvent, by brushing, spraying or soaking to the surface. The concentration of the solution or suspension is not particularly limited, but preferably, it is 0.0001% (1 µg/ml)–0.1% (1 mg/ml), and more preferably 0.0001–0.01%. The solvent is then removed by evaporation. Preferred solvent includes alcohols containing 1–4 carbon atoms or a mixed solvent made of lower alcohols and water. Particularly preferable are aqueous C1-4 alcohols, for example 50–90% methanol, ethanol, propanol and the like in water. Use of lower alcohols that have bacteriocidin activity allows use of culture vessels made of relatively wide range of materials and makes their handling easier, since additional sterilization is not required after coating.

In an preferred embodiment, 1 ml of 70% ethanol solution containing a 0.01% (100 µg/ml in total amount) polymer is added to a culture vessel or a carrier, for example to 35 mm diameter dish so as to cover its inner surface, and then the dish is allowed to stand in a clean bench in order to evaporate the ethanol completely.

In case where the polymer is insoluble in a lower alcohol, it may be suspended or dissolved in such an organic solvent as benzene, dioxane and N,N-dimethylformamide and the like, and the solution is applied over the inner surface of a culture vessel or the surface of carriers and the solvent is removed by evaporation before the vessel is subjected to sterilizing treatment by autoclaving or by γ-rays irradiation. In this case solvent-resistant or thermoresistant water-insoluble polymers and culture vessels are employed.

Especially when the polymer is a natural polymer, it is required to select the solvent and method of sterilization so that the polymer will not lose its cell adhesive activity by decomposition or denaturation. For example, when fibronectin is used for coating, it is dissolved in PBS(−) (phosphate buffered saline without $Ca^{2+}$ or $Mg^{2+}$) to a specified concentration, sterilized by filtration through a membrane filter with pore size of 0.20–0.45 µm, immediately added to the culture vessel, and then the vessel is allowed to stand at 37° C. for more than 15 minutes. The vessel is washed with PBS(−) immediately before use.

According to the present invention, the culture vessels may be a multitray, a dish or a bottle made of glass, polystyrene, polycarbonate, polyethylene, polypropylene or other materials. The inner surface of the culture vessels is sterilized by a conventional method previous to the coating. In case of plastic vessels, it is desirable to be subjected to the plasma treatment in order to make the inner surface to be hydrophilic.

In another embodiment, carriers coated with the coating the polymer having cell adhesive activity may be used for culture of adhesive cells. According to this embodiment, it is possible to increase greatly the area where cells adhere so that a mass culture of cells can be effected in a relatively small volume of a medium.

The carriers that may be used for this purpose are, for example, fine particles or thin leaves of glass, various synthetic resins and ceramics. The shape and size of these carriers depend on the method and scale of culture and are not particularly specified, but it is noted that in suspension culture, for example, size and specific gravity of the carrier should be selected so that gentle agitation or circulation of the medium can keep the carrier in suspension.

As a fine particle carrier, particles of the polymer which can be obtained by suspension polymerization of the aforementioned polymerizable monomers chemically modified with peptides and another monomers may be used. The size of the particles of this type of polymer is ordinarily in the range of 100 µm–5 mm and preferably 100 µm–250 µm.

According to the serum-free culture method of the present invention, a conventional basal medium for animal cell culture to which at least serum albumin is added is used as a serum-free medium.

Referring to a case where the animal adhesive cells are vascular endothelial cells, the following basal media for culture of animal cells may be used singly or in mixture in appropriate ratios: BME, D-MEM, MEM alpha, Eagle MEM, M199, F-10, F-12 and RPMI1641 (see "Manual for Cell Culture," ed. by Koshu Munemura, Kodansha, pp. 110–115, May, 1982), MCDB107 (see Catalog of Kyokuto Seiyaku Kogyo Co.), MCDB131 (see Knedler, A. and Ham, R. G., In Vitro Cellular & Developmental Biology, 23, 7: 481—481 (1987)), MCDB152 and MCDB153 (see "Growth and Differentiation of Mammary Epithelial Cells in Culture," Japan Scientific Societies Press, pp. 72–73, 1987), E-BM (see Catalog of Kurashiki Boseki Co.) and so on. The basal medium may be selected depending on the species of animal and site of blood vessel from which the cells to be cultured are derived.

The medium MCDB 131 comprises 2.67 mg/L of L-Alanine, 63.20 mg/L of L-Arginine.HCl, 2.67 mg/L of L-Alanine, 63.20 mg/L of L-Arginine.HCl, 15.01 mg/L of L-Asparagine.H$_2$O, 13.31 mg/L of L-Aspartic acid, 35.13 mg/L of L-Cysteine.HCl-H$_2$O, 4.41 mg/L of L-Glutamic acid, 1461.50 mg/L of L-Glutamine, 2.25 mg/L of Glycine, 41.93 mg/L of L-Histidine.HCl.H$_2$O, 65.58 mg/L of L-Isoleucine, 131.27 mg/L of L-Leucine, 181.65 mg/L of L-Lysine.HCl, 14.92 mg/L of L-Methionine, 33.04 mg/L of L-Phenylalanine, 11.51 mg/L of L-Proline, 31.53 mg/L of L-Serine, 11.91 mg/L of L-Threonine, 4.08 mg/L of L-Tryptophan, 18.12 mg/L of L-Tyrosine, 117.15 mg/L of L-Valine, 0.00733 mg/L of D-Biotin, 0.602 mg/L of Calcium folinate.5H$_2$O, 0.002063 mg/L of α-Lipoic acid, 6.11 mg/L of Nicotinamide, 11.91 mg/L of D-Pantothenic acid (hemi-Ca salt), 2.056 mg/L of Pyridoxine.HCl, 0.003764 mg/L of Ribmg/L oflavin, 3.373 mg/L of Thiamine.HCl, 0.01355 mg/L of Vitamine B$_{12}$, 0.1351 mg/L of Adenine, 13.96 mg/L of Choline chloride, 1000.00 mg/L of D-Glucose, 7.21 mg/L of i-Inositol, 0.0001611 mg/L of Putrescine, 110.04 mg/L of Sodium pyruvate, 0.02422 mg/L of Thymidine, 235.23 mg/L of CaCl$_2$.2H$_2$O, 298.20 mg/L of KCl, 2463.8 mg/L of MgSO4.7H$_2$O, 6430.0 mg/L of NaCl, 134.04 mg/L of Na$_2$HPO$_4$.7H$_2$O, 0.001248 mg/L of CuSO$_4$.5H$_2$O, 0.2780 mg/L of FeSO$_4$.7H$_2$O, 0.000241 mg/L of MnSO$_4$.5H$_2$O, 0.00371 mg/L of (NH$_4$)$_6$Mo$_7$O$_{24}$.H$_2$O, 0000713 mg/L of NiCl$_2$.6H$_2$O, 0.00387 mg/L of H$_2$SeO$_3$, 2.842 mg/L of NaSiO$_3$.9H$_2$O, 0.000585 mg/L of NH$_4$VO$_3$, 0.0002875 mg/L of ZnSO$_4$.7H$_2$O, 1176.0 mg/L of NaHCO$_3$, 12.42 mg/L of Phenol red (Sodium salt).

The medium MCDB 107 comprises 8.909 mg/L of L-Alanine, 210.7 mg/L of L-Arginine.HCl, 15.07 mg/L of L-Asparagine.H$_2$O, 13.31 mg/L of L-Aspartic acid, 8.78 mg/L of L-Cysteine.HCl, 14.71 mg/L of L-glutamic acid, 365.3 mg/L of L-Glutamine, 22.521 mg/L of Glycine, 20.97 mg/L of L-Histidine.HCl.H$_2$O, 3.939 mg/L of L-Isoleucine, 13.12 mg/L of L-Leucine, 36.54 mg/L of L-Lysine HCl, 4.476 mg/L of L-Methionine, 4.956 mg/L of L-Phenylalanine, 34.53 mg/L of L-Proline, 10.51 mg/L of l-Serine, 11.91 mg/L of L-Threonine, 2.042 mg/L of L-Tryptophan, 5.436 mg/L of L-Tyrosine, 11.72 mg/L of L-Valine, 0.0073 mg/L of Biotin, 0.0006 mg/L of Folinic acid, 0.0021 mg/L of Lipoic acid, 6.105 mg/L of Nicotinamide, 0.2383 mg/L of Pantothenate Ca, 0.062 mg/L of Pyridoxine.HCl, 0.113 mg/L of Ribmg/L oflavin, 0.337 mg/L of Thiamine.HCl, 0.136 mg/L of Cyanocobalamine, 25.32 mg/L of Choline ditertrate, 18.02 mg/L of Inositol, 4.0437 mg/L of Adenine.SO$_4$, 0.0028 mg/L of Linoleic acid, 0.00016 mg/L of Putrescine.2HCl, 0.0727 mg/L of Thymidine, 6640.08 mg/L of NaCl, 149.12 mg/L of KCl, 111 mg/L of CaCl$_2$, 120.33 mg/L of MgSO$_4$, 720.64 mg/L of Glucose, 110 mg/L of Sodium Pyruvate, 408.3 mg/L of KH$_2$PO$_4$, 0.00025 mg/L of CuSO$_4$, 1.39 mg/L of FeSO$_4$.7H$_2$O, 0.00024 mg/L of MgSO$_4$.7H$_2$O, 0.00124 mg/L of (NH$_4$)$_6$Mo$_7$O$_{24}$.4H$_2$O,0.00012 mg/L of NiCl$_2$.6H$_2$O, 0.00387 mg/L of Na$_2$SeO$_3$, 0.061 mg/L of NaSiO$_3$, 0.000113 mg/L of SnCl$_2$.2H$_2$O, 0.000585 mg/L of NH$_4$VO$_3$, 0.144 mg/L of ZnSO$_4$.7H$_2$O, 1.242 mg/L of Phenol red.

Serum albumin is one kind of proteins present in serum, and it has been reported that the serum albumin in serum-free culture enhances the growth of animal cells, and improves long-period subculture of fibroblast cells. (Nilausen, S.: J. Cell Physiol., 96, pp. 1–14 (1978)). It is known that serum albumin enhances the cell growth by controlling the supply of fatty acids to cells, thus working as the carrier for long-chain unsaturated fatty acids.

In the culturing method of the present invention, serum albumins obtained from sera of bovine, horse, and human being, for example, may be used preferably. However, a bovine serum albumin (BSA) is particularly desirable in view of price and risks for example due to virus infection.

When vascular endothelial cells are cultured in serum-free condition according to the present invention, the amount of serum albumin used differs depending on animal species and site of blood vessel from which the cells are derived. For example, in culturing of a human umbilical vein endothelial cell, serum albumin is added into the medium in an amount of 1–1000 µg/ml, preferably 100 µg/ml. When serum albumin is added in less than 1 µg/ml, the growth rate of the cells decreases and the cultured cells are difficult to be maintained. By contrast, addition of more than 1000 µg/ml of the albumin is not desirable since removal of, a protein, i.e. a serum albumins, requires troublesome procedures in isolating the substances secreted by the cells after the culture.

According to the serum-free culture of the present invention, transferrin may be preferably added to the medium. Transferrin is a glycoprotein that transfers Fe$^{3+}$, and augments the cell growth promoting action by providing cells with Fe efficiently. The amount of transferrin added is 1–1000 µg/ml, preferably 1–100 µg/ml. When the amount of transferrin is less than 1 µg/ml, the growth rate of the cells decreases and the cultured cells are difficult to be maintained. Use of more than 1000 µg/ml of transferrin is not desirable since, in addition to high prices of the transferrin, its removal requires troublesome operations in isolating some substances secreted by the cells after the culture.

According to the serum-free culture of the present invention, the medium may further contain antibiotics, various growth factors, hormones and the like that are employed in conventional cell cultures, if desired.

Such antibiotics which may be used in the present invention includes those conventionally used in an animal cell culture, such as gentamicin, amphotericin, ampicillin, mitomycin, kanamycin, penicillin, streptomycin, gentacin, tylosin and aureomycin. The antibiotic is added into the culture medium in a rate of 0.1 µg/ml–100 µg/ml, more preferably in 0.25 µg/ml–50 µg/ml.

As the growth factors and hormones, those that have hitherto been used in culturing vascular endothelial cells and other animal cells may be mentioned. Concretely they are cyclic AMP (cAMP), cartilage-derived growth factor (CDGF), endothelial cell growth factor (ECGF), endothelial cell growth supplement (ECGS), eye-derived growth factor (EDGF), epithelial growth factor (EGF), acidic fibroblast growth factor (acidic FGF), basic fibroblast growth factor (basic FGF), brain-derived fibroblast growth factor (brain FGF), insulin-like growth factor-I (IGF-I), interleukin-1 (IL-1), macrophage-derived growth factor (MDGF), platelet-derived endothelial cell mitogen (PDECM), tumor vessel neogenesis factor (TAF), platelet-derived vascular endothelial cell growth factor (45K-GF), bovine brain extract (BBE), bovine pituitary extract (BPE), human serum-derived thrombin, insulin, glucocorticoid (hydrocortisone, cortisone, corticosterone, dexamethasone, triamcinolone, prednisolone and others), cholesterol, heparin, heparan-sulfuric acid, high density lipoprotein (HLD) and various vitamins. They may be added into the medium singly or in mixture as required.

According to the present invention, the kind of growth factors employed and their amount are difference depending on animal species and site of blood vessel from which the cells to be cultured are derived. For example, in culturing of human umbilical vein endothelial cells, EGF, hydrocortisone, insulin and BBE, in addition to serum albumin and transferrin, are preferably added to the basal medium. When desired, α-tocopherol, cholesterol, and the like may be further added to the medium.

The vascular endothelial cells to be cultured by the method for serum-free culture of the present invention, may be of the cells isolated from various sites of blood vessel of a variety of animal species, thus not particularly limitative. The culturing conditions for vascular endothelial cells are explained above, and basically similar conditions may be employed for culturing other animal adhesive cells including such normal cells as fibroblast, epidermal keratinocyte, bronchial epithelial cell, vascular smooth muscle cell, nerve cell, glia cell, mammary gland epithelial cell, liver parenchymal cell and corneal epithelial cell, and such tumor and established cells as glioma cell, glioblastoma cell and fibrosarcoma cell. However, since preferable basal media are known for the respective cells, the culture conditions may be selected based on them.

In the method for serum-free culture of the present invention, animal adhesive cells are cultured under serum-free conditions in a culture vessel coated with a polymer having cell adhesive activity. The cells can be cultured directly in a serum-free environment even if they are secondarily cultured cells under low serum conditions or cells freshly isolated from an animal. Accordingly, the troublesome process, such as the amount of serum in the culture medium is decreased gradually is not required. Thus, if an established cell or normal cell that has been cultured in a medium containing serum is transplanted directly into a serum-free medium, and there can be developed its normal growth. The animal adhesive cell cultured by the method of the present invention will show not only nearly the same degree of growth as the cell cultured in a medium containing serum but also maintain its various cellular functions.

EXAMPLES

The present invention is explained in more detail with reference to examples thereof.

Synthesis of cell adhesive peptides

The peptides of RGDV (Arg-Gly-Asp-Val), DGEA (Asp-Gly-Glu-Ala) and YIGSR (Tyr-Ile-Gly-Ser-Arg) were synthesized by the ordinary solution method.

Figure 1:
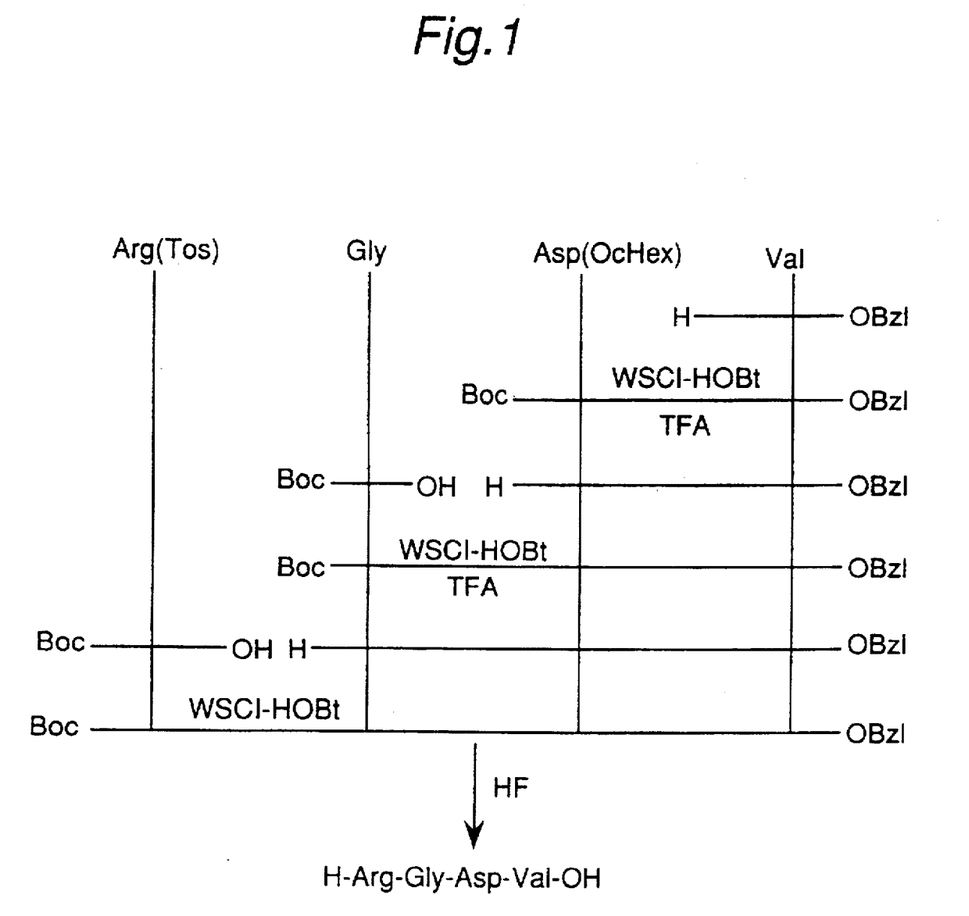
FIG. 1 shows a scheme for synthesis of cell adhesive peptide RDGV.

A scheme for synthesis of the cell adhesive peptide RGDV (Arg-Gly-Asp-Val) by solution method is shown in FIG. 1. Boc-Asp(OcHex) and Val-OBzl, which is a C-terminal group of RGDV peptide, were condensed by the WSCI-HOBt method and the Boc group was removed using trifluoroacetic acid (TFA). Then, Boc-Gly and Asp(OcHex)-Val-OBzl were condensed in the similar way, removed the Boc group and finally Boc-Arg(Tos) and Gly-Asp(OcHex)-Val-OBzl were condensed followed by treatment with anhydrous hydrogen fluoride (HF) treatment to obtain desired RGDV (Arg-Gly-Asp-Val) peptide.

In the same manner as with the RGDV peptide, DGEA and YIGSR peptides were synthesized from their respective component amino acids.

Synthesis of polymers having cell adhesive activity i) The RGDV peptide that had been synthesized previously (0.5 g) and 0.5 g of N-methacryloyloxysuccinimide were dissolved in 2.5 ml of N,N'-dimethylformamide (DMF) and the mixture was stirred overnight at room temperature. To the reaction mixture, 1.0 g of 2-hydroxyethyl methacrylate, 0.5 g of n-butyl methacrylate and 1 ml of DMF were added. After the addition of 20 mg of α,α'-azobisisobutyronitrile as an initiator, the mixture was heated under nitrogen stream at 65° C. for 15 hours. Then the reaction solution was dropped into 5 liters of distilled water under vigorously stirring to obtain a white viscous polymer.

Then, the polymer was dissolved in methanol and was dropped again into 5 liters of distilled water under vigorously stirring. The same procedure was repeated 3 times. The compound was filtered with suction and dried in vacuo at 40° C. to obtain polymer [I] having cell adhesive activity as crystalline powder.

A part of the polymer [I] was hydrolyzed in 6N hydrochloric acid at 166° C. for 30 minutes and submitted to amino acid analysis to confirm that 17.9 µg of RGDV peptide had been introduced into 1 mg of the polymer. The mean molecular weight was 50000.

ii) Polymer [II] having cell adhesive activity was obtained according to the same way as polymer [I] except using 0.1 g of RGDV peptide. Amino acid analysis showed that in 1 mg of the polymer [II], 2.1 µg of RGDV peptide was introduced.

iii) Polymer [III] having cell adhesive activity was obtained according to the same way as polymer [I] except that RGDV peptide was replaced by 0.1 g of DGEA peptide. Amino acid analysis showed that in 1 mg of the polymer [III], 3.0 µg of DGEA peptide was introduced. The mean molecular weight was 59000.

iv) Polymer [IV] having cell adhesive activity was obtained according to the same way as polymer [I] except that RGDV peptide was replaced by 0.1 g of YIGSR peptide. Amino acid analysis showed that in 1 mg of the polymer [IV], 2.4 µg of YIGSR peptide was introduced.

Preparation of culture dishes (i) Polymer [I] was dissolved in 70% (v/v) ethanol to prepare a 0.01% (w/v) (100 µg/ml) solution. One ml of the solution was added into commercially available 35 mm diameter polystyrene dish for cell culture (of which the inner surface was plasma treated to be hydrophilic; Sumitomo Bakelite Co.) and allowed to stand in a clean bench overnight to evaporate the solvent completely. Then a dish (a) coated with the polymer [I] was obtained.

(ii) Collagen type I (Cellmatrix-IC; Nitta Gelatin) was dissolved in 70% ethanol to prepare a 0.01% (w/v) solution. The solution was applied into the 35 mm polystyrene dish and evaporate the solvent in the same manner as in dish (a) to obtain a dish (b) coated with collagen type I.

(iii) The ethanol solutions of the polymer [I] and collagen type I obtained above in (i) and (ii) were mixed in a ratio of 1:1. The mixed solution there obtained was used to coat the 35 mm polystyrene dish in the same manner as in dish (a) to obtain a dish (c) that was coated with a mixture of polymer [I] and collagen type I.

(iv) Synthetic polymers [II]–[IV] were dissolved in 70% ethanol to prepare 0.01% solutions in the same manner as in (i). Each of the solutions was mixed with the solution of collagen type I obtained in (ii) in a ratio of 1:1, and the mixed solutions were applied to the 35 mm polystyrene dishes in the same manner as in dish (a) to obtain dishes (d)–(f), each of which was coated with a mixture of one of the synthetic polymers [II]–[IV] and collagen type I respectively.

(v) As a control, non-coated dish (g) was used.

Example 1

Cells for culture

The normal human umbilical vein endothelial cells (HUVEC) obtained from the culture kit (Endocell kit, Kurashiki Boseki Co., Ltd.) which were secondarily cultured in a low serum medium for growth of vascular endothelial cells (E-GM UV, Kurashiki Boseki Co., Ltd.) were used. E-GM UV was a medium made by adding to a basal medium for vascular endothelial cells (E-BM) an epithelial growth factor (EGF, 10 µg/ml), hydrocortisone (1 µg/ml), antibacterial agents (Gentamicin, 50 µg/ml; amphotericin, 0.25 µg/ml) and bovine brain extract (BBE, 0.4% v/v).

Serum-free media

As the basal medium, MCDB131 medium (prepared according to Knedler, A. and Ham, R. G.: In Vitro Cellular & Developmental Biology, 23, 7: pp. 481—481 (1987)) was used. To this medium, EGF (10 ng/ml, made by Kurashiki Boseki Co.), hydrocortisone (1 µg/ml, Kurashiki Boseki Co.), antibiotics (gentamicin: 50 µg/ml, amphotericin B: 0.25 µg/ml, Kurashiki Boseki Co.), BBE (0.4% v/v, Kurashiki Boseki Co.) and insulin (10 µg/ml, Sigma Co.) were added. Bovine serum albumin (BSA, Sigma Co.) and transferrin (Sigma Co.) were also added in concentrations shown in Table 1 to prepare serum-free media A–D.

TABLE 1

| Serum-free medium | A | B | C | D |
|---|---|---|---|---|
| BSA (µg/ml) | 100 | 100 | 1000 | 0 |
| Transferrin (µg/ml) | 10 | 100 | 10 | 0 |

Cell Culture

Two ml each of the serum-free media shown in Table 2 was added to dishes (a), (b), (c) and (g) which had been prepared by the above-described procedures, and the dishes were incubated in a $CO_2$ incubator at 37° C. over 2 hours. HUVEC that had been suspended in MCDB131 in a concentration of $4.6 \times 10^5$ cells/ml was added to each of the dishes in a volume of 100 µl so as to make each dish contain0 5000 cells/cm². After culturing for 3 hours in the $CO_2$ incubator at 37° C., shapes of the cultured cells were observed under a phase contrast microscope and counted the number of adhered cells. The initial adhesion rate was calculated from the following equation:

Initial adhesion rate (%)=(number of adhered cells/ number of inoculated cells)×100

The results are shown in Table 2.

TABLE 2

| | Initial adhesion rate (%) | | |
|---|---|---|---|
| | Serum-free medium | | Serum-added medium |
| Dish, coated with | A–C | D | (E-GM UV) |
| (a) polymer I | 89–94 | 71 | |
| (b) collagen type I | 92–96 | 77 | |
| (c) polymer I + collagen | 91–97 | 77 | |
| (g) Non-coated | 39–60 | 32 | 100 |

When (a)–(c) dishes were employed, the initial adhesion rate of HUVEC in each dish was close to 100% in any of the serum-free media of A–C to which BSA and transferrin were added. On the other hand, when the serum-free medium D to which BSA and transferrin were not added was used, the initial adhesion rate of HUVEC was considerably lower showing that the addition of BSA and transferrin to the medium is essential in the culturing method of the present invention. In the non-coated dish (g), cultivation in the serum-free media gave very low initial adhesion rates.

Observation under a phase contrast microscope showed that in any of the coated dishes, the cells were adhered and spread on the inner surface of the dishes well. By contrast, in the non-coated dish, not only the initial adhesion rate of the cells was low but also agglomeration of the cells in the central part of the dish was observed. This agglomeration is thought to be due to that the adhesion between cell and dish is weaker than that among cells in the non-coated dish. It is well understood that by coating the dish with natural and/or synthetic polymers having cell adhesive activity the adhesive and spreading activities of cells onto the inner surface of dish is improved.

Example 2

In the same way as in Example 1, HUVEC was cultured for 5 days and the number of viable cells was counted. The results are shown in Table 3.

TABLE 3

| | Number of viable cells ($\times 10^4$/ml) after 5 days' culture Serum-free medium | | | |
|---|---|---|---|---|
| Dish, coated with | A | B | C | D |
| (a) polymer I | 0.58 | 0.73 | 0.95 | 0.22 |
| (b) Collagen type I | 1.49 | 1.96 | 2.41 | 0.38 |
| (c) polymer I + collagen | 1.88 | 2.56 | 2.98 | 0.45 |
| (g) Non-coated | 0.08 | 0.36 | 0.31 | 0.00 |

With the use of a serum-free medium containing BSA and transferrin and a culture vessel coated with a synthetic polymer or collagen type I, HUVEC could be maintained at least for several days. In the dish (c) that was coated with a mixture of a polymer [I] and collagen a prominent growth of cells was observed.

On the other hand, the growth of HUVEC was not observed in the serum-free medium without BSA or transferrin. The results of Examples 1 and 2 clearly show that the addition of serum albumin and transferrin is essential in the method for serum-free culture of vascular endothelial cells of the present invention.

Example 3

Serum-free media

As the basal media, MCDB131 and MCDB107 (Kyokuto Seiyaku Kogyo Co.) were used. EGF (10 ng/ml), hydrocortisone (1 μg/ml), antibiotics (gentamicin: 50 μg/ml, amphotericin B: 0.25 μg/ml), BBE (0.4%, v/v), insulin (10 μg/ml), transferrin (10 μg/ml) and different concentrations of bovine serum albumin (BSA) were added to both of the media respectively to prepare a series of serum-free media.

Cell Culture

In the same way as in Example 1, HUVEC was cultured in each of the dishes (a)–(c) with the media containing various concentration of BSA. The number of cells was counted after 5 days' culture. The results are shown in Table 4.

TABLE 4

| | Number of cells (× $10^4$/ml) after 5 days' culture BSA concentration (μg/ml) | | | | | | | | | |
|---|---|---|---|---|---|---|---|---|---|---|
| | 1000 | | 100 | | 10 | | 1 | | 0 | |
| | 131 | 107 | 131 | 107 | 131 | 107 | 131 | 107 | 131 | 107 |
| Serum-free basal medium Dishes coated with | | | | | | | | | | |
| (a) Polymer I | 1.21 | 0.44 | 0.58 | 0.36 | 0.66 | 0.33 | 0.46 | 0.26 | 0.41 | 0.29 |
| (b) collagen type I | 2.56 | 2.54 | 1.36 | 1.19 | 1.08 | 1.01 | 1.02 | 0.60 | 1.14 | 0.66 |
| (c) Polymer I + collagen type I | 3.08 | 2.06 | 2.02 | 1.77 | 1.56 | 1.33 | 1.60 | 0.77 | 1.18 | 0.71 |

Cell growth was observed in the serum-free media to which BSA was added. In particular, greatly enhanced growth was observed when more than 1 μg/ml, and preferably more than 100 μg/ml of BSA was added. On the other hand, in the medium to which BSA was not added the growth rate was low and in some cases cultured cells could not be maintained.

Example 4

Serum-free medium

As the basal medium, MCDB131 was employed. Into the medium, EGF (10 ng/ml), hydrocortisone (1 μg/ml), antibiotics (gentamicin: 50 μg/ml, amphotericin B: 0.25 μg/ml), BBE (0.4%, v/v), insulin (10 μg/ml), transferrin (10 μg/ml) and BSA (100 μg/ml) were added to prepare a serum-free medium.

Cell Culture

HUVEC was cultured in the same manner as in Example 1 with the dish (b) coated with collagen type I and dishes (c)–(f) coated with mixtures of collagen type I and polymers [I] to [IV] respectively. The cell number was counted after culturing for 5 days. The results are shown in Table 5.

TABLE 5

| Dish | Cell number (× $10^4$/cm$^2$) |
|---|---|
| (c) Polymer I + collagen | 2.38 |
| (d) Polymer II + collagen | 2.26 |

TABLE 5-continued

| Dish | Cell number (× $10^4$/cm$^2$) |
|---|---|
| (e) Polymer III + collagen | 2.41 |
| (f) Polymer IV + collagen | 2.15 |
| (b) Collagen type I | 1.53 |
| (g) Non-coated | 0.33 |

It is obvious that when cultured in the dishes coated with a mixture of any of the synthetic polymers [I]–[IV] and collagen type I, the growth of HUVEC increased significantly than coated with collagen type I singly.

Example 5

Production of endothelin by cultured normal human umbilical vein endothelial cell was studied.

After HUVEC was cultured for 5 days in a serum-free medium used in Example 4, the whole medium was replaced by a fresh one and cultivation was continued for further 24 hours. Then, the culture supernatant was isolated and the amount of endothelin contained in the supernatant was determined. As a control, the amount of endothelin produced by the HUVEC that was cultured in the medium E-GM UV containing 2% fetal bovine serum in (b), (c) and (g) dishes were estimated. Estimation of endothelin-1 estimation kit (Kokusai Shiyaku Kogyo Co.). The results are shown in Table 6.

TABLE 6

| Medium | Dish coated by | Cell number on the 6th day ($\times 10^4$/cm$^2$) | Amount of endothelin produced | |
|---|---|---|---|---|
| | | | (pg/dish/day) | (pg/$10^4$ cells) |
| Serum-free medium | (c) Polymer I + collagen | 2.69 | 723 | 269 |
| | (d) Polymer II + collagen | 2.81 | 766 | 273 |
| | (e) Polymer III + collagen | 2.72 | 798 | 293 |
| | (f) Polymer IV + collagen | 2.68 | 715 | 267 |
| | (b) Collagen type I | 2.26 | 618 | 273 |
| | (g) Non-coated | 0.25 | 0 | 0 |
| Serum-added medium (2%) | (c) Polymer I + collagen | 3.78 | 1256 | 332 |
| | (b) Collagen type I | 4.05 | 1209 | 299 |
| | (g) Non-coated | 3.25 | 1105 | 340 |

It was found that the vascular endothelial cells cultured by the serum-free method of the present invention maintain similar potency of endthelin production per cell as that of the cells cultured in a medium containing serum.

What is claimed is:

1. A method for culturing human vascular endothelial cells in serum free condition comprising 1) coating at least one polymer having cell adhesive activity to adhere cells to a surface on at least a part of an inner surface of a culture vessel of surface of a carrier for cell culture, wherein said at least one polymer is a synthetic polymer modified with a peptide having cell adhesive activity, or a natural polymer having cell adhesive activity, or a combination thereof, and 2) culturing the human vascular endothelial cells in the coated vessel or with the coated carrier using a serum-free medium for human vascular endothelial cell culture containing at least (i) serum albumin isolated from serum, (ii) transferrin, (iii) hydrocortisone, and (iv) epithelial growth factor whereby initial adhesion of said cells to said polymer coating and viability of said cells are increased.

2. A method as claimed in claim 1, wherein the polymer having cell-adhesive activity is a mixture of the natural polymer and the synthetic polymer modified with a peptide having cell adhesive activity.

3. The method as claimed in claim 1, wherein the natural polymer is selected from the group consisting of collagen, gelatin, keratin, fibronectin, vitronectin, and laminin.

4. The method as claimed in claim 1, wherein the peptide having cell adhesive activity is selected from the group consisting of Arg-Gly-Asp-Val, Arg-Gly-Asp-Ser, Arg-Gly-Asp-Asn, Asp-Gly-Glu-Ala, Tyr-Ile-Gly-Ser-Arg, and mixtures thereof.

5. The method as claimed in claim 1, wherein the serum-free medium comprises a basal medium selected from the group consisting of MCDB 131 and MCDB 107, wherein medium MCDB 131 comprises 2.67 mg/L of L-Alanine, 63.20 mg/L of L-Arginine.HCl, 2.67 mg/L of L-Alanine, 63.20 mg/L of L-Arginine .HCl, 15.01 mg/L of L-Asparagine $H_2O$, 13.31 mg/L of L-Aspartic acid, 35.13 mg/L of L-Cysteine.HCl-$H_2O$, 4.41 mg/L of L-Glutamic acid, 1461.50 mg/L of L-Glutamine, 2.25 mg/L of Glycine, 41.93 mg/L of L-Histidine.HCl.$H_2O$, 65.58 mg/L of L-Isoleucine, 131.27 mg/L of L-Leucine, 181.65 mg/L of L-Lysine.HCl, 14.92 mg/L of L-Methionine, 33.04 mg/L of L-Phenylalanine, 11.51 mg/L of L-Proline, 31.53 mg/L of L-Serine, 11.91 mg/L of L-Threonine, 4.08 mg/L of L-Tryptophan, 18.12 mg/L of L-Tyrosine, 117.15 mg/L of L-Valine, 0.00733 mg/L of D-Biotin, 0.602 mg/L of Calcium folinate.5$H_2O$, 0.002063 mg/L of $\alpha$-Lipoic acid, 6.11 mg/L of Nicotinamide, 11.91 mg/L of D-Pantothenic acid (hemi-Ca salt), 2.056 mg/L of Pyridoxine.HCl, 0.003764 mg/L of Ribmg/L oflavin, 3.373 mg/L of Thiamine.HCl, 0.01355 mg/L of Vitamine $B_{12}$, 0.1351 mg/L of Adenine, 13.96 mg/L of Choline chloride, 1000.00 mg/L of D-Glucose, 7.21 mg/L of i-Inositol, 0.0001611 mg/L of Putrescine, 110.04 mg/L of Sodium pyruvate, 0.02422 mg/L of Thymidine, 235.23 mg/L of $CaCl_2.2H_2O$, 298.20 mg/L of KCl, 2463.8 mg/L of $MgSO4.7H_2O$, 6430.0 mg/L of NaCl, 134.04 mg/L of $Na_2HPO_4.7H_2O$, 0.001248 mg/L of $CuSO_4.5H_2O$, 0.2780 mg/L of $FeSO_4.7H_2O$, 0.000241 mg/L of $MnSO_4.5H_2O$, 0. 00371 mg/L of $(NH_4)_6Mo_7O_{24}.H_2O$, 0000713 mg/L of $NiCl_2.6H_2O$, 0.00387 mg/L of $H_2SeO_3$, 2.842 mg/L of $NaSiO_3.9H_2O$, 0.000585 mg/L of $NH_4VO_3$, 0.0002875 mg/L of $ZnSO_4.7H_2O$, 1176.0 mg/L of $NaHCO_3$, 12.42 mg/L of Phenol red (Sodium salt); and MCDB 107 comprises 8.909 mg/L of L-Alanine, 210.7 mg/L of L-Arginine.HCl, 15.07 mg/L of L-Asparagine.$H_2O$, 13.31 mg/L of L-Aspartic acid, 8.78 mg/L of L-Cysteine.HCl, 14.71 mg/L of L-Glutamic acid, 365.3 mg/L of L-Glutamine, 22.521 mg/L of Glycine, 20.97 mg/L of L-Histidine.HCl.$H_2O$, 3.939 mg/L of L-Isoleucine, 13.12 mg/L of L-Leucine, 36.54 mg/L of L-Lysine HCl, 4.476 mg/L of L-Methionine, 4.956 mg/L of L-Phenylalanine, 34.53 mg/L of L-Proline, 10.51 mg/L of l-Serine, 11.91 mg/L of L-Threonine, 2.042 mg/L of L-Tryptophan, 5.436 mg/L of L-Tyrosine, 11.72 mg/L of L-Valine, 0.0073 mg/L of Biotin, 0.0006 mg/L of Folinic acid, 0.0021 mg/L of Lipoic acid, 6.105 mg/L of Nicotinamide, 0.2383 mg/L of Pantothenate Ca, 0.062 mg/L of Pyridoxine.HCl, 0.113 mg/L of Ribmg/L oflavin, 0.337 mg/L of Thiamine.HCl, 0.136 mg/L of Cyanocobalamine, 25.32 mg/L of Choline ditertrate, 18.02 mg/L of Inositol, 4.0437 mg/L of Adenine.$SO_4$, 0.0028 mg/L of Linoleic acid, 0.00016 mg/L of Putrescine.2HCl, 0.0727 mg/L of Thymidine, 6640.08 mg/L of NaCl, 149.12 mg/L of KCl, 111 mg/L of $CaCl_2$, 120.33 mg/L of $MgSO_4$, 720.64 mg/L of Glucose, 110 mg/L of Sodium Pyruvate, 408.3 mg/L of $KH_2PO_4$, 0.00025 mg/L of $CuSO_4$, 1.39 mg/L of $FeSO_4.7H_2O$, 0.00024 mg/L of $MgSO_4.7H_2O$, 0.00124 mg/L of $(NH_4)_6Mo_7O_{24}.4H_2O$, 0.00012 mg/L of $NiCl_2.6H_2O$, 0.00387 mg/L of $Na_2SeO_3$, 0.061 mg/L of $NaSiO_3$, 0.000113 mg/L of $SnCl_2.2H_2O$, 0.000585 mg/L of $NH_4VO_3$, 0.144 mg/L of $ZnSO_4.7H_2O$, 1.242 mg/L of Phenol red.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:1:

Arg Gly Asp Val
   1

( 2 ) INFORMATION FOR SEQ ID NO:2:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:2:

Arg Gly Asp Ser
   1

( 2 ) INFORMATION FOR SEQ ID NO:3:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:3:

Arg Gly Asp Asn
   1

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:4:

Asp Gly Glu Ala
    1

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:5:

Tyr Ile Gly Ser Arg
    1                    5